United States Patent [19]

Yoneyama

[11] Patent Number: 4,633,888
[45] Date of Patent: Jan. 6, 1987

[54] ELECTROTHERAPEUTICAL DEVICE

[75] Inventor: Takeshi Yoneyama, Yokohama, Japan

[73] Assignee: Nippon Athletic Industry Company, Tokyo, Japan

[21] Appl. No.: 727,605

[22] Filed: Apr. 26, 1985

Related U.S. Application Data

[63] Continuation of Ser. No. 471,676, Mar. 3, 1983, abandoned.

[30] Foreign Application Priority Data

Nov. 27, 1982 [JP] Japan .................................. 57-208054

[51] Int. Cl.⁴ ............................................... A61N 1/28
[52] U.S. Cl. .................................... 128/784; 128/798; 128/802; 128/419 R
[58] Field of Search ............... 128/783, 784, 798, 799, 128/802, 804, 303.18, 379, 384, 389, 391, 392, 419 R

[56] References Cited

U.S. PATENT DOCUMENTS

| 504,336 | 9/1983 | Ekholm | 128/392 |
| 658,027 | 9/1900 | Steiger | 128/391 X |
| 3,957,053 | 5/1976 | Woo | 128/329 A X |
| 4,142,521 | 3/1979 | Konikoff | 128/82.1 |
| 4,173,229 | 11/1979 | Halfon | 128/419 R |
| 4,319,584 | 3/1982 | McCall | 128/784 |

Primary Examiner—Lee S. Cohen
Attorney, Agent, or Firm—Young & Thompson

[57] ABSTRACT

An electrotherapeutical device, comprising an electrically insulating substrate, a semiconductor element having photoelectromotive force and thermoelectromotive force and which is adhered to the substrate, and lead wires, one end of each lead wire being connected to the semiconductor element and the other end thereof being formed into a terminal, has a very small size, can be easily arranged on a desired portion of a human body, and can produce a therapeutical effect.

1 Claim, 20 Drawing Figures

FIG_1a
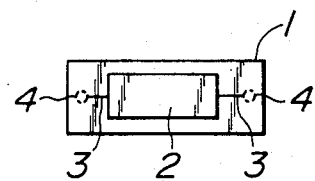
FIG_1b
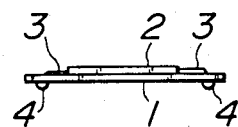
FIG_1c
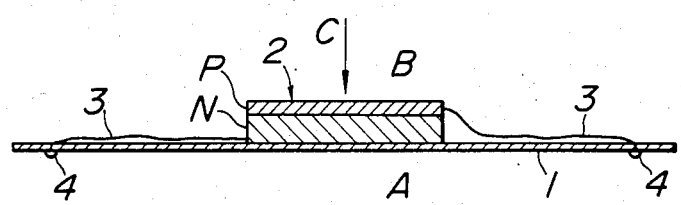
FIG_1d
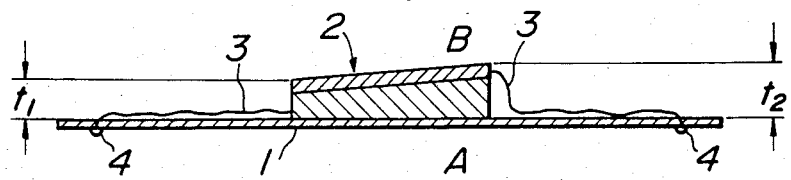

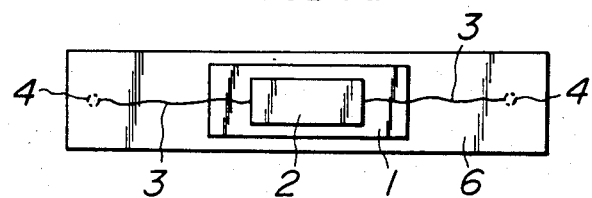
FIG_4a
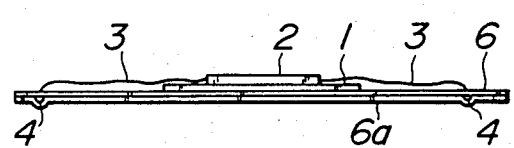
FIG_4b
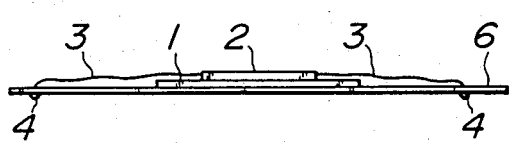
FIG_4c
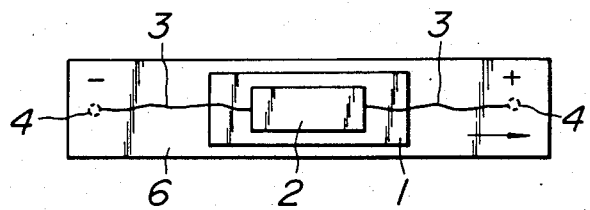
FIG_5a
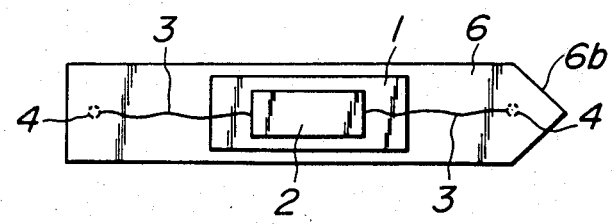
FIG_5b

FIG_6a
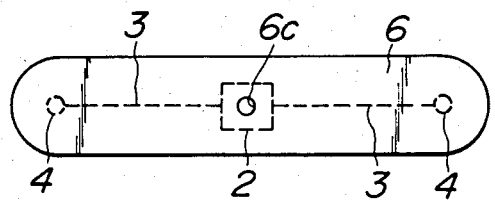
FIG_6b
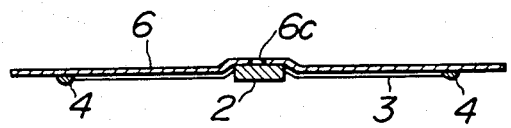
FIG_6c
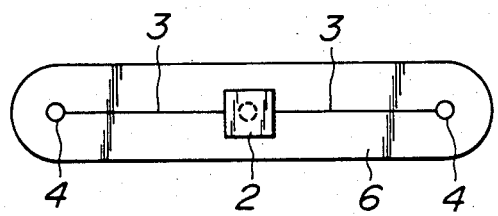

FIG_9

ELECTROTHERAPEUTICAL DEVICE

This application is a continuation of application Ser. No. 471,676, filed Mar. 3, 1983, now abandoned.

BACKGROUND OF THE INVENTION (1) Field of the Invention

The present invention relates to an electrotherapeutical device using electricity in the medical treatment for a disease of a human body.

(2) Description of the Prior Art

It is commonly known that when a very small amount of electric current is flowed through a human body, a certain therapeutical effect appears. Particularly, when electric stimulus is given to keiraku or keiketsu ("keiraku" and "keiketsu" are effective spots in acupuncture), which are present at various portions of a human body, circulation of blood can be improved, stiffness of muscles can be relieved, pain can be removed, and other therapeutical effects can be attained.

As the device for carrying out such electrotherapeutics, various devices have hitherto been proposed. However, all of them have a large size, and electrotherapeutics must be carried out in a hospital or home having the electrotherapeutical device.

SUMMARY OF THE INVENTION

The present invention aims to solve the above described drawbacks of conventional electrotherapeutical devices.

The object of the present invention is to provide a very small size electrotherapeutical device, which can be stuck to a desired portion of a human body at any time and in any place in a simple manner and can attain a therapeutical effect, by utilizing a semiconductor element having photoelectromotive force and thermoelectromotive force generated by light and heat, such as a semiconductor element made of silicon, germanium or the like.

Thus the present invention comprises an electrotherapeutical device, comprising an electrically insulating substrate; a semiconductor element having photoelectromotive force and thermoelectromotive force and being adhered to the surface of the substrate; and lead wires, one end of each lead wire being connected to the semiconductor element, and the other end thereof being formed into a terminal so as to be in contact with a human body.

BRIEF DESCRIPTION OF THE DRAWINGS

FIG. 1a is a plan view of a first example of the electrotherapeutical device of the present invention;

FIG. 1b is a front view of the device illustrated in FIG. 1a;

FIG. 1c is an enlarged sectional view of the device illustrated in FIG. 1a;

FIG. 1d is an enlarged sectional view of a modification of the device illustrated in FIG. 1a;

FIG. 2b is a front view of the device illustrated of FIG. 2a;

FIG. 3b is a front view of the device illustrated in FIG. 3a;

FIG. 4a is a plan view of a fourth example of the electrotherapeutical device of the present invention;

FIG. 4b is a front view of the device illustrated in FIG. 4a;

FIG. 4c is a front view of the device illustrated in FIG. 4a after a release paper has been peeled off the device;

FIGS. 5a and 5b are plan views of other examples of the electrotherapeutical device of the present invention;

FIG. 6a is a plan view of a further example of the electrotherapeutical device of the present invention;

FIG. 6b is a front view of the device illustrated in FIG. 6a;

FIG. 6c is a view of the lower surface of the device illustrated in FIG. 6a.

DESCRIPTION OF THE PREFERRED EMBODIMENT

Figure 2A:
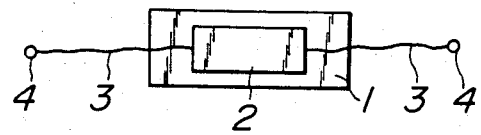
FIG. 2a is a plan view of a second example of the electrotherapeutical device of the present invention.
Figure 2B:
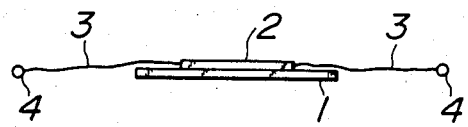

The present invention will be explained in more detail referring to the drawings.

In the drawings, the numeral 1 represents a substrate made of ceramic plate, Bakelite plate, mica, thick paper or the like and having electrically insulating property; the numeral 2 represents a semiconductor element having photoelectromotive force and thermoelectromotive force; the numeral 3 represents a thin lead wire, such as an enameled wire or the like; and the numeral 4 represents a terminal formed by making the end of the lead wire 3 into a round shape, or by subjecting the wire end to soldering, gold plating or the like.

The electrotherapeutical device of the present invention is assembled in the following manner. A semiconductor element 2 having photoelectromotive force and thermoelectromotive force is adhered to the surface of an electrically insulating substrate 1, and lead wires 3 are connected at one end to both ends of the semiconductor element 2 and are formed into terminals 4 at the other end so as to be in contact with a human body.

In the first example of the electrotherapeutical device illustrated in FIG. 1a, lead wires 3 penetrate through a substrate 1 from its surface to its back surface at both end portions, and terminals 4 are formed at the protruding portions of the lead wires 3.

FIG. 1a is a plan view of the above described device of the first example; FIG. 1b is a front view of the device; FIG. 1c is an enlarged sectional view of the device; and FIG. 1d is an enlarged sectional view of a modification of the device. That is, as illustrated in FIGS. 1c and 1d, a semiconductor element 2 having photoelectromotive force and thermoelectromotive force has one P-N junction. When light strikes the semiconductor element 2 as indicated by an arrow C in FIG. 1c, a photoelectromotive force is generated between the left and right terminals 4. The photoelectromotive force is represented by the following formula (1).

$$V_{AB}\alpha(kT/e) \ln (I_L/I_0) \tag{1}$$

In the formula
  $I_L$: photoelectric current
  $I_0$: dark current
  $k/e$: constant
  $T$: temperature Even when the semiconductor element 2 is not explosed to light the element 2 is in contact with a human body at its A side and is influenced by the body temperature. When the element 2 is cooled by the air at its B side, a temperature difference is established between A and B, and a thermoelectromotive force is generated between A and B.

When the thickness t of the semiconductor element 2 is varied from $t_1$ to $t_2$ ($t_2 > t_1$) as illustrated in FIG. 1d, a temperature difference is established between both ends of the semiconductor element 2 as well, and hence a thermoelectromotive force is generated as well. The thermoelectromotive force $\theta_{AB}$ is represented by the following formula (2).

$$\theta_{AB} \alpha (kT/e) \ln (nB/nA) \qquad (2)$$

In the formula
nA, nB: electron concentration
k/e: constant
T: temperature

It was found from experiments that a photoelectromotive force of as high as about DC 200 mV was generated by an irradiated luminous intensity of 800 luxes in a silicon semiconductor element. By contrast, in a dark place at night, photoelectromotive force was not generated, but a thermoelectromotive force of about DC 40 mV was generated by the difference between the body temperature and the air temperature.

Thus, when an electrotherapeutical device of the present invention is arranged at a desired place on a human body, the above described photo- and thermo-electromotive forces act percutaneously upon the human body and give electric stimulus thereto, and various therapeutical effects can be attained.

In the device of the second example illustrated in FIG. 2a, lead wires 3 having a greater length are used, whereby terminals 4 are arranged outside a substrate 1. In the device of the third example illustrated in FIG. 3a, a needle 5 is connected to each of the terminals 4 of the device illustrated in FIG. 2a.

In the device of the fourth example illustrated in FIG. 4a, an adhesive tape 6 having a release paper 6a is adhered to the lower surface of a substrate 1, and the terminal 4 of the lead wire 3 protrudes to the adhesive surface side of the adhesive tape 6. Accordingly, when the release paper 6a is peeled off, the terminal 4 is exposed.

It is advantageous that the adhesive tape 6 be marked with symbols (+) and (−) or with an arrow in order to represent the polarity of the terminals 4 as illustrated in FIG. 5a. Furthermore, the end portion 6b of the adhesive tape 6 may be formed into a triangular shape as illustrated in FIG. 5b in order to indicate the direction of the polarity.

In the device illustrated in FIG. 6a, the above described semiconductor element 2, lead wires 3 and terminals 4 are directly adhered to the lower surface of an adhesive tape 6. The reference 6c represents a hole formed through the substrate 1 so as that light can strike directly upon the element 2.

Figure 7:
FIGS. 7-10 are explanative views illustrating how to use the electrotherapeutical device of the present invention.

An explanation will be made how to use the electrotherapeutical device having the above described structure according to the present invention. The device of the first example illustrated in FIG. 1a is arranged at a desired place on a human body, for example, as illustrated in FIG. 7, and both the end portions of the substrate 1 are adhered to the human body by means of an adhesive tape 7.

When a device is arranged on a human body in the above described manner, an electric voltage generated in the semiconductor element 2 having photoelectromotive force and thermoelectromotive force upon the reception of light or generated therein due to the temperature difference even in the absence of light is applied between the terminals 4 on both sides of the device, and a very small amount of electric current flows in the human body to provide a therapeutical effect.

Figure 8:
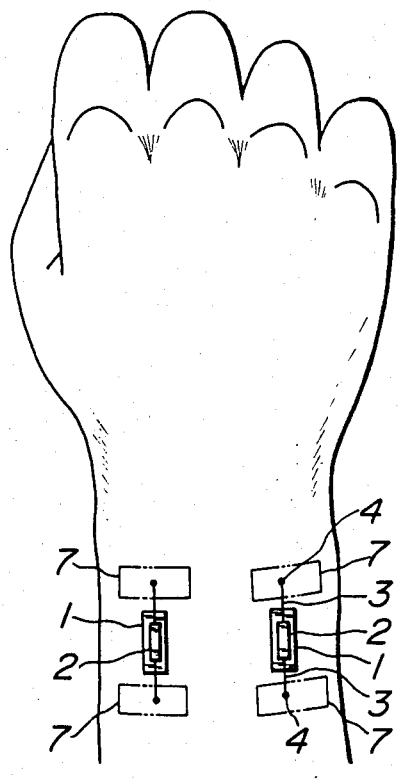

The device of the second example illustrated in FIG. 2a is used, for example, as illustrated in FIG. 8. This device has lead wires 3 having a length greater than that of the lead wires of the device of the first example, and therefore this device has the advantage over the device of the first example that this device is larger in the distance between the terminals 4 than the device of the first example.

Figure 3A:
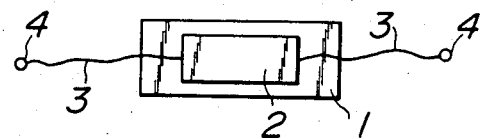
FIG. 3a is a plan view of a third example of the electrotherapeutical device of the present invention.
Figure 3B:
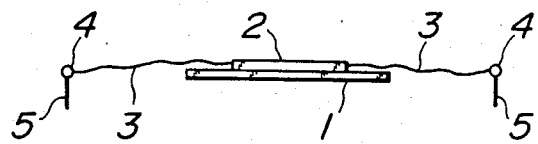

The device of the third example illustrated in FIG. 3a can be applied to a human body by merely sticking into the human body a needle 5 connected to each terminal 4. The use method of this device is the same as that of the device of the second example, except the sticking of the needles.

Figure 9:
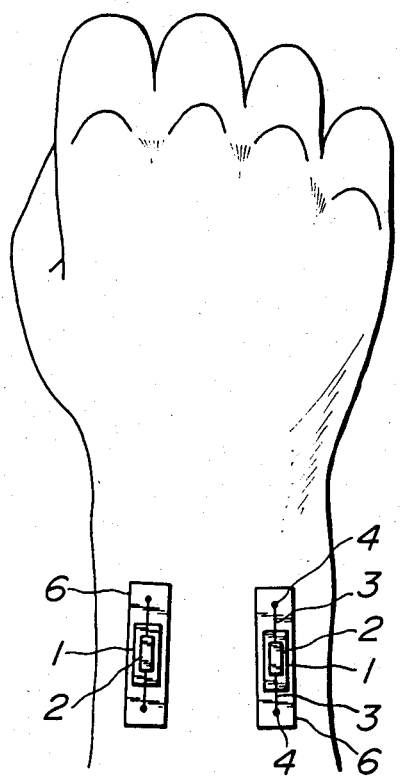

When the device of the fourth example illustrated in FIG. 4a is used, a release paper 6a adhered to the adhesive tape 6 is firstly peeled off as illustrated in FIG. 4c, and then the device is adhered to a desired part of a human body by means of the adhesive tape 6 as illustrated, for example, in FIG. 9. The devices illustrated in FIGS. 5a and 5b are used in the same manner as described in the device illustrated in FIG. 4a.

Figure 10:
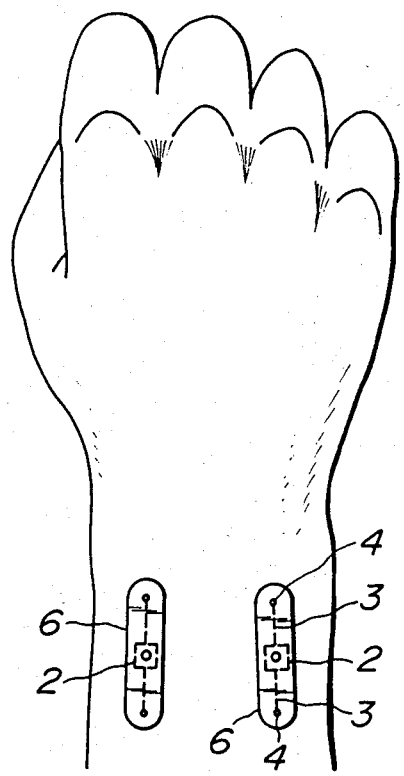

The device illustrated in FIG. 6a has a substrate made of an adhesive tape 6. Therefore, when the device is used, the release paper (not shown) is peeled off similarly to the device illustrated in FIG. 4a, and then the device is adhered to a desired part of a human body as illustrated in FIG. 10.

The electrotherapeutical device of the present invention has a very small size as described above, and therefore the device can be easily adhered to a desired part of a human body. Moreover, this electrotherapeutical device itself is provided with a semiconductor element 2 having photoelectromotive force and thermoelectromotive force, which are the electric power supply source, and therefore the device can generate an electromotive force to give continuous and percutaneous electric stimulus to a human body either when light strikes the device or when the device is placed in a dark place out of the light. Furthermore, the electrotherapeutical device of the present invention can be used for a long period of time, and therefore even if the electromotive force generated by the semiconductor element 2 having photoelectromotive force and thermoelectromotive force is very small, the device can attain a sufficiently high therapeutical effect.

What is claimed is:

1. An electrotherapeutical device having high therapeutical effect, comprising a substrate in the form of a small sheet of electrically insulating material having a first surface adapted to be placed upon the human body and an opposed second surface; a semiconductor element having both photoelectromotive force and thermoelectromotive force which is in the form of a sheet which is smaller than said sheet of electrically insulating material and which is adhered to said second surface of the substrate; and a pair of lead wires, one end of each lead wire being connected to the semiconductor element and the other end thereof being formed into a terminal so as to be in contact with a human body, the lead wires being connected to the semiconductor element at opposite ends of the semiconductor element, the two terminals of the lead wires being spaced apart so as to contact a human body at two spaced points, and needles connected to the terminals of the respective lead wires, whereby heat from said human body, conducted through said electrically insulating material to said semiconductor element, generates an electrical current that is applied through said wires and needles to said human body.

* * * * *